US011536789B2

(12) United States Patent
Weinberg et al.

(10) Patent No.: US 11,536,789 B2
(45) Date of Patent: Dec. 27, 2022

(54) HYBRID MULTIFERROIC NANOPARTICLES AS MRI CONTRAST AGENT FOR SENSING OF ELECTRIC FIELDS IN A HUMAN BODY

(71) Applicant: Weinberg Medical Physics, Inc., North Bethesda, MD (US)

(72) Inventors: Irving Weinberg, North Bethesda, MD (US); Lamar Odell Mair, Baltimore, MD (US); Oleg Udalov, North Bethesda, MD (US)

(73) Assignee: WEINBERG MEDICAL PHYSICS INC, North Bethesda, MD (US)

( * ) Notice: Subject to any disclaimer, the term of this patent is extended or adjusted under 35 U.S.C. 154(b) by 194 days.

(21) Appl. No.: 16/893,047

(22) Filed: Jun. 4, 2020

(65) Prior Publication Data

US 2020/0386837 A1   Dec. 10, 2020

Related U.S. Application Data

(60) Provisional application No. 62/857,080, filed on Jun. 4, 2019.

(51) Int. Cl.
| | |
|---|---|
| *G01R 33/44* | (2006.01) |
| *G01R 33/56* | (2006.01) |
| *A61B 5/055* | (2006.01) |
| *G01R 33/12* | (2006.01) |
| *A61B 5/0515* | (2021.01) |
| *A61K 49/06* | (2006.01) |

(52) U.S. Cl.
CPC ............ *G01R 33/443* (2013.01); *A61B 5/055* (2013.01); *A61B 5/0515* (2013.01); *A61K 49/06* (2013.01); *G01R 33/1215* (2013.01); *G01R 33/1276* (2013.01); *G01R 33/5601* (2013.01)

(58) Field of Classification Search
CPC ............ G01R 33/1215; G01R 33/1276; G01R 33/5601; G01R 33/443; A61K 49/06; A61B 5/0515; A61B 5/055
See application file for complete search history.

(56) References Cited

U.S. PATENT DOCUMENTS

| | | | |
|---|---|---|---|
| 5,203,332 A | 4/1993 | Leunbach | |
| 2011/0311635 A1* | 12/2011 | Stucky | ..................... B01J 13/02 502/344 |
| 2013/0225974 A1 | 8/2013 | Van Den Brink | |
| 2017/0003291 A1 | 1/2017 | Bahado-Singh | |
| 2017/0265927 A1* | 9/2017 | Weinberg | ................ H02J 50/80 |
| 2018/0303373 A1* | 10/2018 | Freeman | ............ G01R 33/4806 |

\* cited by examiner

*Primary Examiner* — Gregory H Curran
(74) *Attorney, Agent, or Firm* — Barnes & Thornburg LLP

(57) ABSTRACT

An apparatus includes a plurality of particles, wherein each particle contains a plurality of magnetizable (for example, ferromagnetic) and ferroelectric materials in fixed physical relationship (for example, physical contact) with one another. A method and apparatus measure magnetic fields arising from or within the plurality of particles.

17 Claims, 5 Drawing Sheets

US 11,536,789 B2

HYBRID MULTIFERROIC NANOPARTICLES AS MRI CONTRAST AGENT FOR SENSING OF ELECTRIC FIELDS IN A HUMAN BODY

PRIORITY AND CROSS REFERENCE

This patent application claims priority to U.S. Provisional Patent Application No. 62/857,080, entitled "HYBRID MULTIFERROIC NANOPARTICLES AS MRI CONTRAST AGENT FOR SENSING OF ELECTRIC FIELDS IN A HUMAN BODY," filed Jun. 4, 2019, the disclosure of which being incorporated herein by reference in its entirety.

FIELD

Disclosed embodiments relate to sensing of electric fields in living tissues for diagnostic purposes and for BRAIN-machine interfaces.

BACKGROUND

Conventional Magnetic Resonance Imaging (MRI) does not collect information about electrical fields in a sample. However, when a contrast agent (for example, gadolinium-based gadoterate meglumine) is introduced into a sample, THE time-dependent change in local magnetization caused by the presence of the contrast agent can be used to determine which portions of the sample are reached by the contrast agent. Nevertheless, the distribution of contrast agent is unaffected by electric fields.

Nonetheless, many neurologic functions in living tissues are transmitted or otherwise mediated by localized electric fields. However, it is possible to measure electrical currents with special MRI methods, but only for currents in the MICROAMPERE range (see, for example, "Synchronized Detection of Minute Electrical Currents using Lorentz Effect Imaging", by T-K Truong, J. L. Wilbur, and A. W. Song, published in Journal of Magnetic Resonance 2006 1791): 85-91) (incorporated by reference in its entirety), which is at least ten times higher than the typical currents produced by small neuronal bundles or single neurons.

Moreover, there are optically-active CONTRAST agents which can be used in laboratory animals to detect neuronal electrical fields, but these are not used in humans or large animals because of the scattering of light from the neuron to detectors mounted on the surface of the head.

SUMMARY

Disclosed embodiments provide an apparatus that includes a plurality of particles, wherein each particle contains a plurality of magnetizable (for example, ferromagnetic) and ferroelectric materials in fixed physical relationship (for example, physical contact) with one another.

In accordance with disclosed embodiments, a method and apparatus measure magnetic fields arising from or within the plurality of particles. In accordance with at least one embodiment, the mechanism for measuring magnetic fields may be a magnetic resonance imaging (MRI) instrument or a magnetometer. In accordance with at least one embodiment, the mechanism may include a magnetic particle imaging instrument that monitors the magnetic state of particles. Effectively, the instruments can thereby non-invasively detect electric fields (for example, from a neuron or group of neurons) by having the instruments monitor the magnetic states near or in the plurality of particles

BRIEF DESCRIPTION OF THE FIGURES

The detailed description particularly refers to the accompanying figures in which.

DETAILED DESCRIPTION

Figure 1:
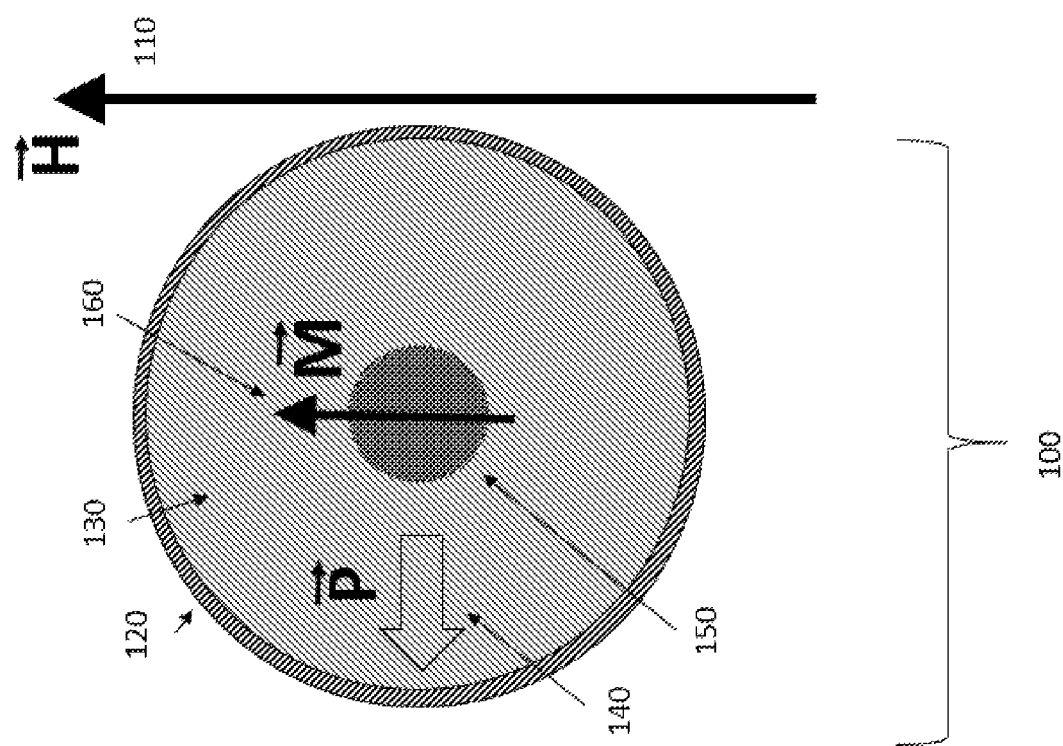
FIG. 1 shows a configuration of the disclosed embodiments wherein at least one particle, and each particle, contain a combination of ferromagnetic materials and ferroelectric materials.

FIG. 1 shows a configuration of an apparatus 100 provided in accordance with the disclosed embodiments wherein at least one particle, and each particle, contains a combination of ferromagnetic materials and ferroelectric materials. The positions of the ferromagnetic and ferroelectric components within the particle are stable with respect to one another.

For the purposes of this disclosure, we define this mechanical stability to mean that the ferromagnetic and ferroelectric components cannot be repositioned with respect to each other by mechanical mechanisms after the particle has been fabricated. However, mechanical strains may still be exerted by one component on another.

For the purposes of this disclosure, the term "particle" implies a structure that is less than 1,000 microns in maximal diameter, and more than 5 nanometers in maximal diameter. The FIG. 1 configuration shows an equilibrium orientation of the magnetic moment 160 of the ferromagnetic component 150 of the particle 100 when placed in an externally-applied magnetic field (represented by a vector labeled with vector notation "H") 110. The magnitude of the externally-applied magnetic field H may be low (for example, 1 gauss) or may be high (for example, 10 teslas), or may be in between those values.

It should be understood that the term "externally-applied field" means a field applied from outside of the particle, for example, from a magnetic resonance instrument (not shown) disposed near a structure containing the particle 100. The structure may be a body part in a living organism, or tissue in a body part of a living organism or may be an electronic component.

In configuration 100, the particle may have a coating 120 of a slippery material that facilitates rotation and/or transport of the particle in tissue or in other environments. For example, coating 120 may be polyethylene glycol. Coating 120 may be sufficiently slippery to allow rotation of one or more of the internal portions of the particle without rotation of the entire particle. Particle 100 contains a ferroelectric volumetric structure 130, which is represented by a sphere in FIG. 1, but may have other shapes (for example, a rod or cube). For the purposes of this disclosure, a ferroelectric material is defined as a material that has a spontaneous electric polarization whose magnitude and/or direction can be affected by the application of an external electric field.

It should be understood that the term "external electric field" means a field applied from outside of the particle, for example, from a neuron, muscle cell, or other cell type or cell component involved in transferring or creating electrical signals or impulses. Ferroelectric volumetric structure 130 has an electric field polarization with vector notation "P" 140.

A magnetizable (for example, ferromagnetic) particle component 150 is shown within the ferroelectric component 130. The ferromagnetic component 150 is shown centrally in FIG. 1, but its location may be non-central (as in FIG. 2) or outside of the ferroelectric component (not shown). The ferromagnetic component 150 has a net magnetic moment that is represented by an arrow 160, 260, 360, 460, 560, 660 and the vector notation "M". In general, the net magnetic moment 160 is aligned with the external magnetic field direction 110 (labeled H). It should be understood that changing the direction of magnetic polarization of magnetizable component 150 does not generally require a very strong imposed magnetic field.

The angle of the electric polarization 140 of the ferroelectric component 130 with respect to the orientation of the magnetic polarization (labeled "M") 160 of the magnetic component 150 may be random, or may be non-random, depending on the process of fabrication of the particle 100. For example, the particle 100 may be "poled" through application of strong external magnetic and/or electric field (s). It should be understood that changing the direction of electric polarization of ferroelectric component 130 with respect to its preferred lattice direction may require a very strong imposed electric field (for example, a megavolt per meter).

Figure 2:
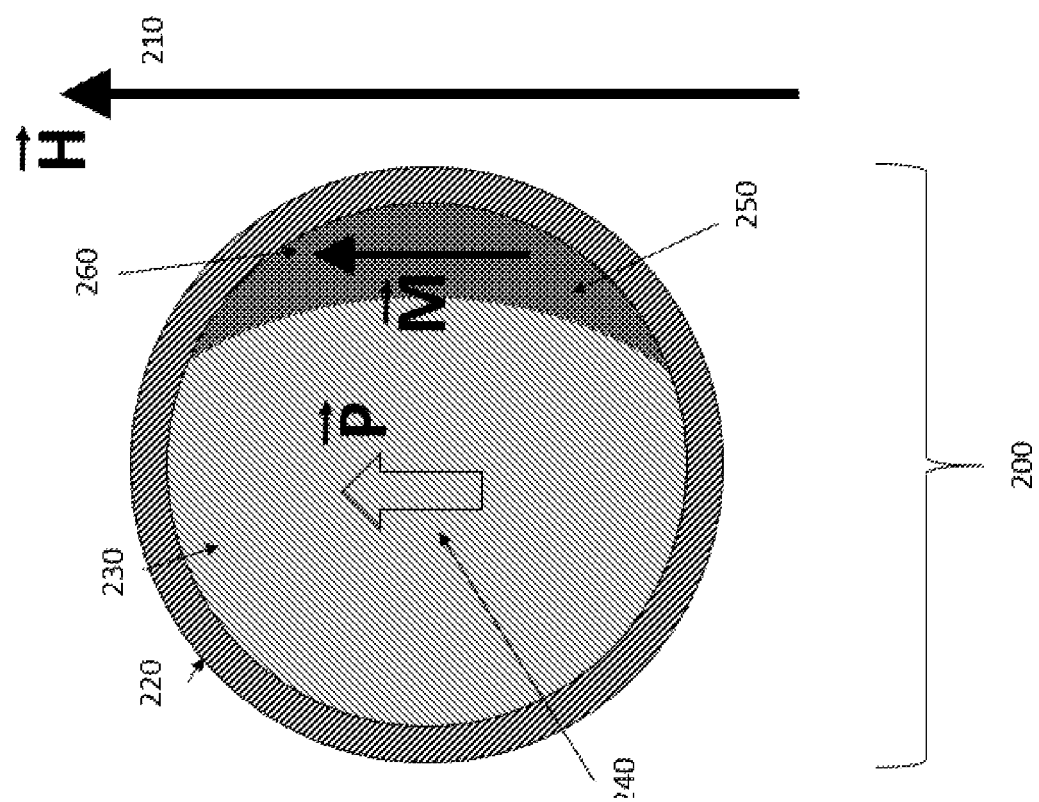
FIG. 2 shows an alternative particle configuration with the same combination of materials as in FIG. 1, but with the ferromagnetic component located in a different position.

FIG. 2 shows an alternative particle configuration 200 with the same combination of materials as in 100, but with the ferromagnetic component 250 located in a different position with respect to the ferroelectric component 230, and with elongation of the ferromagnetic component so that it has a long "easy axis". Again, a coating 220 may be present. The ferromagnetic component has a net magnetic moment that is represented by an arrow 260 and the vector notation "M". It should be understood that changing the direction of the magnetic polarization M 260 is easier (i.e. requires less energy) if the external magnetic field H 210 is in the direction of the magnetizable component's easy axis. The magnitude of magnetic polarization M 260 is maximal when the external magnetic field H 210 is in the direction of the magnetizable component's easy axis 260.

Figure 3:
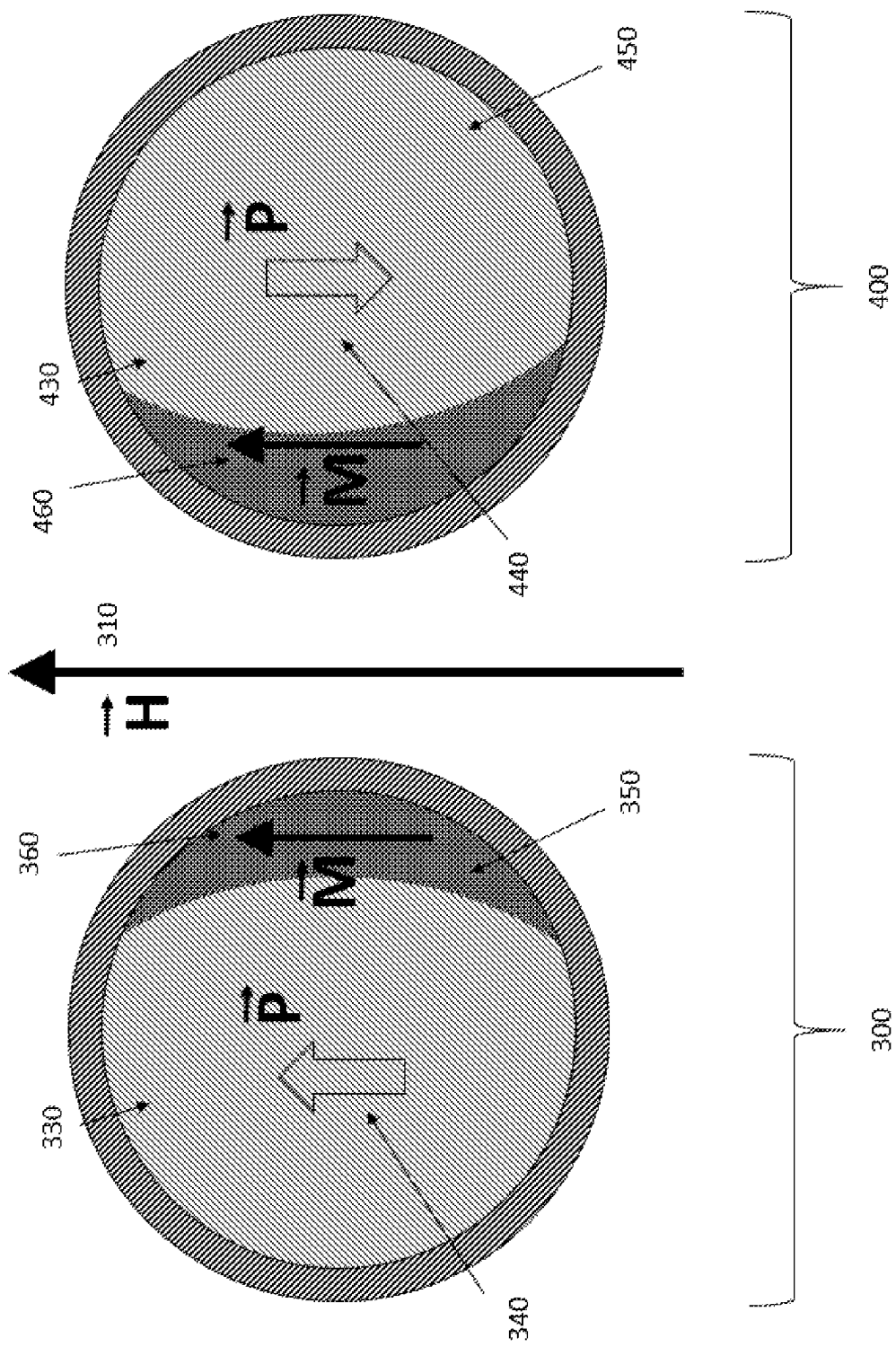
FIG. 3 illustrates an example wherein two particles are exposed to the same external magnetic field H.

FIG. 3 shows two particles 300, 400 exposed to the same external magnetic field H 310. Although only two particles are shown, it is understood that the same principles would apply to a much larger number of particles (for example: a billion particles). Both particles 300 and 400 are similar in composition to the particle shown in FIG. 2.

Similarly, it is understood that the same types of materials are present in similar configurations and proportions (for example, within 10%). No significant external electric field has been applied to the particles, and so the electrical polarizations 340 and 440 are in different orientations with respect to the external magnetic field 310. The magnetic polarizations 360 and 460 are aligned with the external magnetic field 310.

Figure 4:
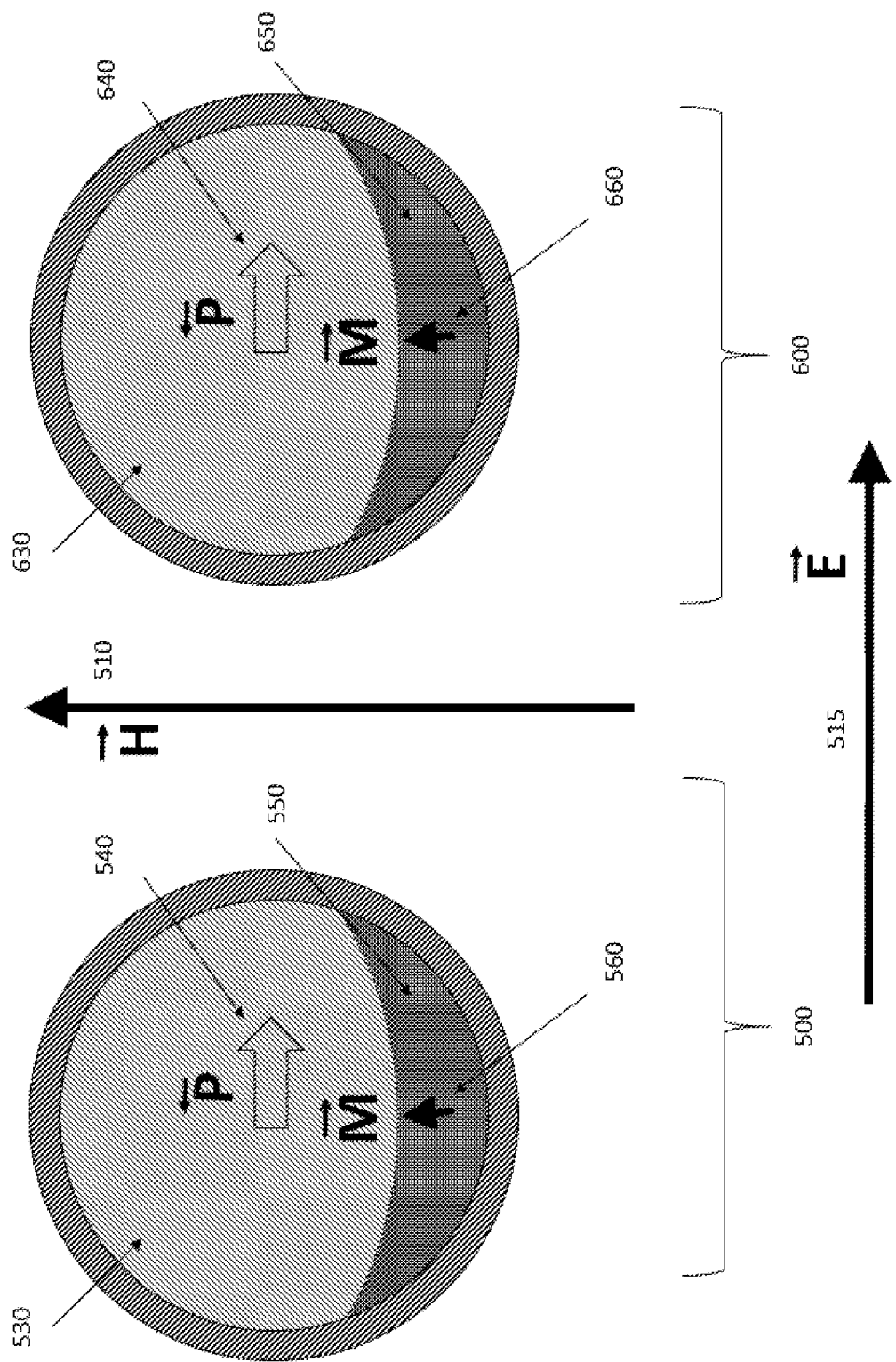
FIG. 4 illustrates an example wherein two particles are exposed to the same external magnetic field H.

FIG. 4 shows two particles 500, 600 exposed to the same external magnetic field H 510. Both particles 500 and 600 are similar to the particle shown in FIG. 2. An external electric field 515) (labeled E) has been applied to the particles, and so the electrical polarizations 540 and 640 are not aligned with respect to the external magnetic field 610. The easy axes of magnetic polarizations 560 and 660 are not aligned with the external magnetic field 510, and so the magnitudes of the net polarization has been reduced from the case of FIG. 3.

Figure 5:
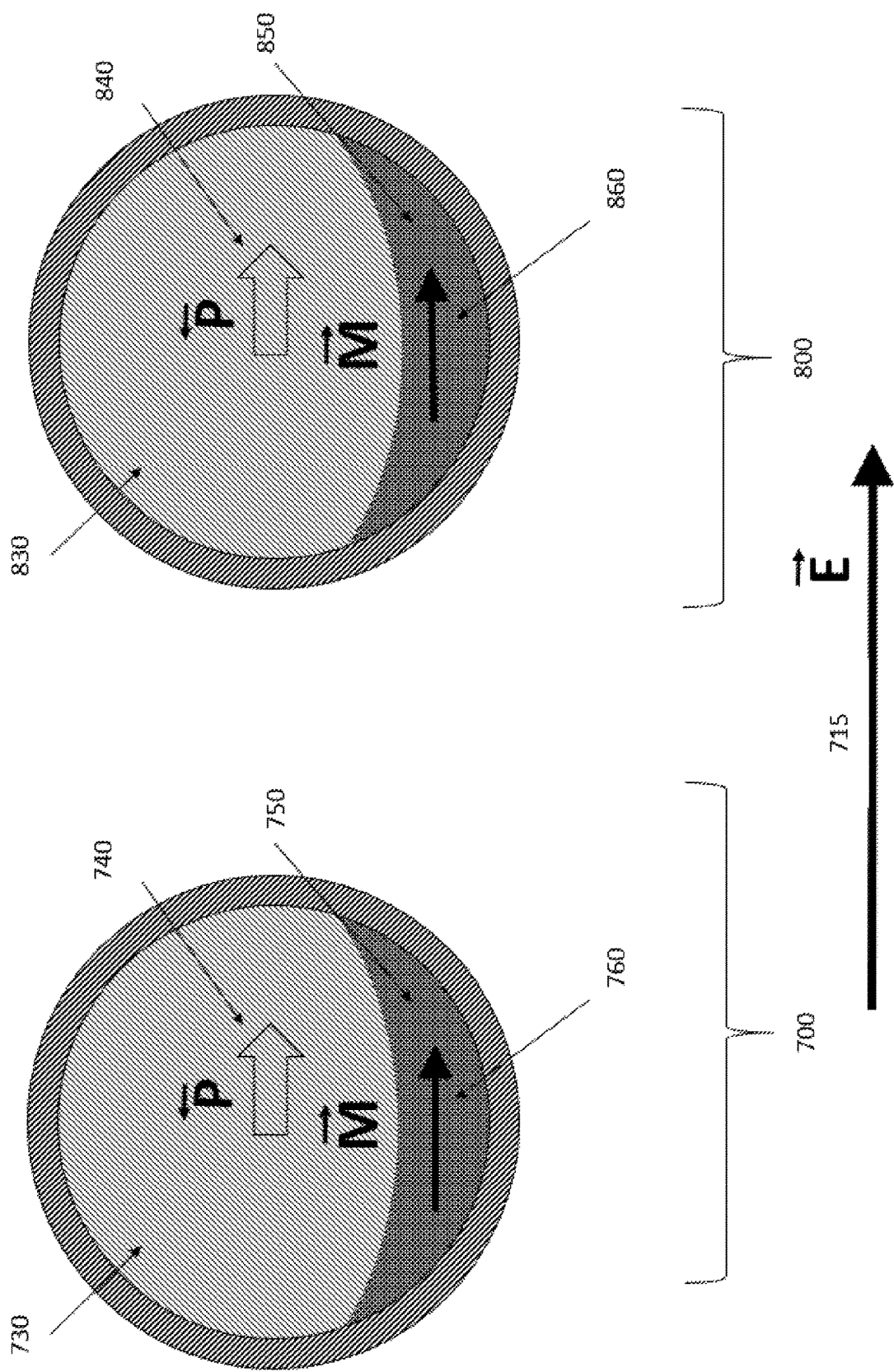
FIG. 5 illustrates an example wherein two particles are not exposed to an external magnetic field.

FIG. 5 shows two particles 700, 800 that are not exposed to an external magnetic field. They may have been exposed to an external magnetic field in the past in order to create magnetizations 760 and 860, or those magnetizations may be spontaneous (for example, due to shape anisotropy). Both particles 700 and 800 are similar to the particle shown in FIG. 2. An external electric field 715) (labeled E) has been applied to the particles, and the electrical polarizations 740 and 840 align with respect to the external electric field. Magnetic polarizations 760 and 860 may add to a net magnetic polarization that may be detected with a monitor of magnetic fields (for example, a magnetometer, not shown).

With this understanding of the figures in mind, it should be understood that the disclosed embodiments provide of an apparatus that includes a plurality of particles 100, 200, 300, 400, 500, 600, each particle containing magnetizable (for example, ferromagnetic) 150 and ferroelectric materials 130 in fixed physical relationship (for example, physical contact) with one another. The method and apparatus include a mechanism for measuring magnetic fields arising from or within the plurality of particles.

In accordance with at least one embodiment, the mechanism is a Magnetic Resonance Imaging (MRI) instrument or a magnetometer. In accordance with at least one embodiment, that mechanism may include a magnetic particle imaging instrument that monitors the magnetic state of particles. Effectively, the instruments can thereby non-invasively detect electric fields (for example, from a neuron or group of neurons) by having the instruments monitor the magnetic states near or in the plurality of particles 100, 200, 300, 400, 500, 600.

The preponderance of alignment of particle magnetizations illustrated in FIG. 4 and FIG. 5 can result in a net local magnetization that may be detected with an external mechanism for measuring local magnetic fields, for example, with a magnetic resonance imaging instrument or magnetometer (not shown). In accordance with at least one embodiment, a change in net local magnetization may be measured (for example, from FIG. 3 to FIG. 4), rather than the actual net local magnetization at any specific time.

It is known that the state of local magnetic fields affects the response of protons or other atomic constituents to radiofrequency electromagnetic fields. For example, the net magnetization of particles may increase the local magnetic inhomogeneity and thereby reduce the decay time of protons that have previously had their spins coherently aligned (for example, as a result of radiofrequency irradiation). An example of such effect is described in the scientific publication entitled "Artificial local magnetic field inhomogeneity enhances T2 relaxivity", by Z. Zhou and others, published in Nature Communications in 2017 (incorporated by reference in its entirety).

It should be understood that external magnetic fields H delivered by the magnetic resonance imaging instrument may be applied quickly enough so that images may be collected before the spins of the protons have had a chance to substantially decay, so that early images represent anatomy and later images represent the effects of electrical fields.

It should be understood that the particles 400, 500, 600, 700 may be rotated with an applied magnetic field, and that the resistance to rotation manifest by an alternation in rotation frequency may serve as a useful measurement of the orientation of the polarization of the ferroelectric component 140. The rotation frequency may be manifest through a Doppler shift in emanations from the particle, for example. Measurement of the polarization orientation may indirectly provide information about the presence and magnitude of local electrical field 515, 715). The ability of the particles to rotate under the application of an external magnetic field may be enhanced through the incorporation of magnetizable rings around the particle, as taught by L. Mair et al in the US patent application 2016/0125994, (incorporated by reference in its entirety).

In accordance with at least one embodiment, the ferroelectric component 130 may be barium titanate. In accordance with at least one embodiment, the barrier for magnetization switching of the ferromagnetic component 150 exceeds thermal energy at room temperature. As an example, elliptical iron ferromagnetic particles with long axis to short axis ratio of order of 3 (e.g., short axis 1 nm and long axis 3.3 nm) will have a shape anisotropy on the order of 500 K, which exceeds room temperature.

Further, it should be understood that the particles 400, 500, 600, 700 may be rotated with an applied electric field. This rotation can be registered via measuring magnetic field produced by the particles using magnetic resonance imaging or other magnetometer. Measuring particles rotation one measures electric field acting on the particles. This electric field can be produced by a studied object (from, for example, brain tissue) or can be an external electric field.

A typical MRI system produces a high magnetic field H 110, for example, in excess of 50 milliteslas. Therefore, the interaction of the external field 110 with magnetic materials is extremely strong. The electric field produced in living tissues is weak, for example, 10 volts per meter at a distance 10 microns from a neuron. In accordance with at least one embodiment, it is possible to have a pronounced influence of the electric field 515) on particles 500, 600 by making the ferroelectric components 530, 630 bigger than the ferromagnetic components 550, 650. For ferromagnetic material 550, 650 with magnetization of order of 1000 gauss, ferroelectric grain with polarization of order of 10 mkmC/cm^2 and magnetic field H of 3000 gauss, the volume of the ferroelectric component 530 may be 10,000 times the volume of the ferromagnetic component 550. This can be achieved for ferromagnetic particles with the size of 3 nm and 200 nm ferroelectric grains.

Although the magnetizable component 250 in FIG. 2 is shown in an eccentric location within a particle 200, it is understood that many different possible configurations of magnetizable component 250 may achieve similar results.

It should be understood that application of magnetic field H 210 may cause the polarization 240 of the ferroelectric component 230 to change. This change may be effected by strain exerted on the ferroelectric component 230 by a change in configuration of the magnetizable component 250. The change may be caused by interactions of the magnetic field H 210 directly on the ferroelectric material 230. For example, component 230 may not be a pure ferroelectric but may have mixed ferroelectric and magnetic properties. One such mixed material is described in the scientific publication entitled "strong magnetoelectric coupling in mixed ferrimagnetic-multiferroic phases of a double perovskite", by M. K. Kim et al, in Scientific Reports 9, article number 5456 2019) (incorporated by reference in its entirety). It should be understood that particles 100, 200, 300, etc.) illustrated may be fabricated of such mixed materials rather than of separate component materials, or of materials with various proportions of constituents with ferroelectric and ferromagnetic or paramagnetic properties. The change in polarization 240 may result in an electric field being applied to tissues, for example, that may lead to stimulation.

It should be understood that particles described in this invention disclosure may be administered to a living being, for example, intra-venously or orally or intra-nasally. It should be understood that the magnetic properties of components of the particles (for example, component 150 may be used to assist in propulsion or transport of the particles within a body or body part. It should be understood that the term body part is used broadly to indicate an entire body part (for example, a brain) or tissues within a body part (for example, neurons), or cells within tissues. Additionally, it is understood that particles described in this invention disclosure may be administered to a sample of living tissue which has been grown, cultured, or removed from a living being, and that such living tissue may be then reinserted into, grafted onto, or transplanted into or onto a living being at some future time. Additionally, it is understood that particles described in this invention disclosure may be administered to non-living tissue and activated so as to provide electrical stimulation to the tissue, which may thereby result in altered electrical signaling arising from the tissue at future times.

Those skilled in the art will recognize, upon consideration of the above teachings, that the above exemplary embodiments may perform the above-specified operations (and those referred in the claims) under the control of at least one controller that may utilize or be based upon use of one or more programmed processors programmed with a suitable computer program. However, the disclosed embodiments could utilize one or more controllers implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Furthermore, it should be understood that control and cooperation of components of an apparatus described above may be provided using software instructions that may be stored in a tangible, non-transitory storage device such as a non-transitory computer readable storage device storing instructions which, when executed on one or more programmed processors, carry out the above-described method operations and resulting functionality. In this case, the term non-transitory is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments of the present invention. Such alternative storage devices should be considered equivalents.

While certain illustrative embodiments have been described, it is evident that many alternatives, modifications, permutations and variations will become apparent to those skilled in the art in light of the foregoing description. While illustrated embodiments have been outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

The invention claimed is:

1. An apparatus for measuring electric fields in a structure, the apparatus comprising:
    a plurality of particles, wherein each particle contains component materials with magnetizable and ferroelectric properties, and the component materials are in fixed relative positions to one another; and
    an instrument sensitive to magnetic fields or to changes of magnetic fields, wherein the instrument is configured to detect change in magnetizations of one or more magnetizable components of the plurality of particles when one or more ferroelectric components in the plurality of particles rotate when exposed to an externally-applied electric field.

2. The apparatus of claim 1, wherein the plurality of particles have been administered to a living being.

3. The apparatus of claim 1, wherein the instrument sensitive to magnetic fields or to changes in magnetic fields is a magnetic resonance imaging device.

4. The apparatus of claim 1, wherein the instrument sensitive to magnetic fields or to changes in magnetic fields is a magnetometer.

5. The apparatus of claim 1, wherein the instrument sensitive to magnetic fields or to changes in magnetic fields is a magnetic particle imaging instrument.

6. The apparatus of claim 1, wherein the plurality of particles are each made of a material with both magnetic and ferroelectric properties that act as if the particles were made of separate magnetic and ferroelectric components.

7. The apparatus of claim 1, wherein each of the plurality of particles are coated with a material that enables rotation of one or more components in a particle or of an entire particle.

8. A method of measuring electric fields in a structure, the method comprising:
    introducing a plurality of particles into or upon the structure, each the particle containing component materials with magnetizable and ferroelectric properties, wherein the component materials in fixed relative positions to one another; and
    detecting, using an instrument sensitive to magnetic fields or to changes of magnetic fields, a change in magnetizations of one or more magnetizable components of the plurality of particles when one or more ferroelectric components in the plurality of particles rotate when exposed to the electric fields within the structure.

9. The method of claim 8, wherein the magnetic properties of the magnetizable components of the particles are used to transport the particles into or within a structure.

10. The method of claim 8, wherein the structure is a body part in a living organism and the instrument collects multiple images that reflect anatomy of the body part and also electric fields within the body part.

11. The method of claim 8, further comprising using the spin decay of protons near particles to assess the magnetization state of the particles.

12. The method of claim 8, wherein the plurality of particles have been administered to a living being.

13. The method of claim 8, wherein the instrument sensitive to magnetic fields or to changes in magnetic fields is a magnetic resonance imaging device.

14. The method of claim 8, wherein the instrument sensitive to magnetic fields or to changes in magnetic fields is a magnetometer.

15. The method of claim 8, wherein the instrument sensitive to magnetic fields or to changes in magnetic fields is a magnetic particle imaging instrument.

16. The method of claim 8, wherein the plurality of particles are each made of a material with both magnetic and ferroelectric properties that act as if the particles were made of separate magnetic and ferroelectric components.

17. The method of claim 8, wherein each of the plurality of particles are coated with a material that enables rotation of one or more components in a particle or of an entire particle.

* * * * *